United States Patent [19]

Bauman

[11] 4,208,401
[45] Jun. 17, 1980

[54] QUATERNARY AMMONIUM ALKYLENE DIPHOSPHONATE ANTI-CALCULUS AGENTS

[75] Inventor: Robert A. Bauman, New Brunswick, N.J.

[73] Assignee: Colgate Palmolive Company, New York, N.Y.

[21] Appl. No.: 945,053

[22] Filed: Sep. 22, 1978

Related U.S. Application Data

[63] Continuation of Ser. No. 825,882, Aug. 19, 1977, abandoned.

[51] Int. Cl.$^2$ ............................ A61K 7/22; C07F 9/38
[52] U.S. Cl. .................................. 424/54; 260/501.12
[58] Field of Search ...................... 424/54; 260/501.12

[56] References Cited

U.S. PATENT DOCUMENTS

| | | | |
|---|---|---|---|
| 2,542,886 | 2/1951 | Wach | 424/54 |
| 2,774,786 | 12/1956 | Erickson | 260/501.12 |
| 3,925,543 | 12/1975 | Donahue | 424/54 |
| 4,054,598 | 10/1977 | Blum et al. | 424/49 |

FOREIGN PATENT DOCUMENTS 2335901  7/1972  Fed. Rep. of Germany ............. 424/54

OTHER PUBLICATIONS

Gross et al., J. Prakt. Chem., 318(1), pp. 116–126, 1976.

*Primary Examiner*—G. T. Breitenstein
*Attorney, Agent, or Firm*—Robert L. Stone; Murray M. Grill; Herbert S. Sylvester

[57] ABSTRACT

Quaternary ammonium alkylene diphosphonates useful as stain-inhibiting, anti-calculus agents, compatible with cationic antimicrobials; the process of preparing said quaternary ammonium diphosphonates; and compositions containing an effective anti-calculus amount of said quaternary diphosphonate admixed with a dental or oral carrier. These compounds are particularly effective in inhibiting tooth staining caused by cationic antimicrobials.

7 Claims, No Drawings

QUATERNARY AMMONIUM ALKYLENE DIPHOSPHONATE ANTI-CALCULUS AGENTS

This is a continuation of application Ser. No. 825,882 filed Aug. 19, 1977, now abandoned.

The present invention relates to quaternary ammonium alkylene diphosphonates and salts thereof, and to a method for the preparation thereof by the hydrolysis of the tetraalkyl phosphonate esters of quaternary ammonium compounds, and to oral preparations containing an effective amount of said anti-calculus agent.

DESCRIPTION OF THE PRIOR ART

Quaternary ammonium phosphonic acid compounds such as quaternary ammonium alkylene monophosphonic acids or salts thereof having the formula:

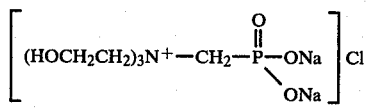

are disclosed in U.S. Pat. No. 3,453,301 by Uhing; and quaternary ammonium trialkylene-triphosphonic acid having the formula:

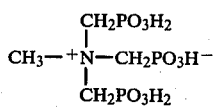

are disclosed in U.S. Pat. No. 3,925,453 by Clarke.

Also disclosed in the prior art are aminoalkylene diphosphonic acid compounds, such as the tertiary amino-alkylene disphosphonates as shown in U.S. Pat. Nos. 3,678,154 by Widder, 3,846,420 by Wollman et al and 3,899,496 by Schindler et al. The Widder patent utilizes his polyphosphonates as anti-calculus agents in dental formulations.

SUMMARY OF THE INVENTION

It has now been discovered that the quaternary ammonium alkylene diphosphonates of this invention are three times more effective than the tertiary aminodiphosphonates disclosed in U.S. Pat. No. 3,678,154 in inhibiting the crystal growth of hydroxyapatite, which is indicative of anti-calculus activity; is compatible with cationic materials such as antimicrobial agents; and exhibits a greater degree of inhibition of tooth staining caused by said cationic antimicrobials.

Accordingly, it is a primary object of this invention to provide stain-inhibiting quaternary ammonium diphosphonates possessing enhanced anti-calculus activity.

Another object of this invention is to provide anti-calculus agents compatible with cationic materials such as antimicrobial agents.

Still another object is to provide anti-calculus agents capable of inhibiting tooth staining associated with cationic antimicrobial agents.

Accordingly, the present invention relates to stain-inhibiting oral compositions, compatible with cationic materials and capable of inhibiting the formation of dental calculus; and to novel quaternary ammonium alkylene diphosphonates represented by the structural formula:

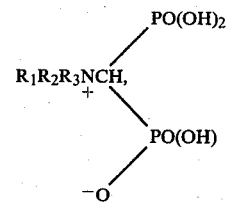

wherein $R_1$, $R_2$ and $R_3$ are each independently an alkyl group containing from 1 to about 20 carbon atoms, or an aralkyl group wherein the aryl radical is a phenyl radical and the alkyl radical contains 1–8 carbon atoms; and pharmaceutically acceptable salts thereof, such as the alkali metals (e.g., sodium and potassium), alkaline earth metals (e.g., calcium, magnesium), ammonium or low molecular weight substituted ammonium (e.g., mono-, di-, and triethanolammonium) salts. The preferred R ($R_1$, $R_2$ and $R_3$) substituents are lower alkyl groups containing 1 to about 6 carbon atoms, since the effectiveness of these compounds is due to the combination of the quaternary nitrogen and the phosphonate groups and not the alkyl groups which are "inert" (ineffective). The higher alkyl groups would dilute the effectiveness of this material due to the additional weight of said compounds.

Oral compositions containing said quaternary alkylene diphosphonates in admixture with cationic antimicrobial agents such as chlorhexidine, benzethonium chloride or cetyl pyridinium chloride effect a greater inhibition of stain and exhibit a greater compatibility therewith than the non-quaternary phosphonates.

The method of preparing the quaternary ammonium alkylene diphosphonates generally comprises hydrolyzing a phosphonate ester containing a quaternary nitrogen such as $$(CH_3)_3N^+CH[PO(OEt)_2]_2X^-$$

(prepared by H. Gross, B. Costisella, W. Burger, J. prakt. Chem. 311 563 (1969), in the presence of a hydrohalide such as hydrobromide acid, at elevated temperatures (reflux), and recovering the corresponding quaternary diphosphonic acid in solution form, precipitating said quaternary diphosphonate with a lower alkanol, dissolving said precipitate in boiling alkanol from which it spontaneously recrystallizes.

More specifically, the quaternary ammonium diphosphonates of instant invention are prepared from known starting materials, tetraethyl trimethylammoniomethylene diphosphonate which may be prepared in accordance with the method described by Gross et al in Angew. Chem. Internat. Edit. 7 391 (1968) and J. prakt. Chem. 311 563 (1969), and represented by the following equations:

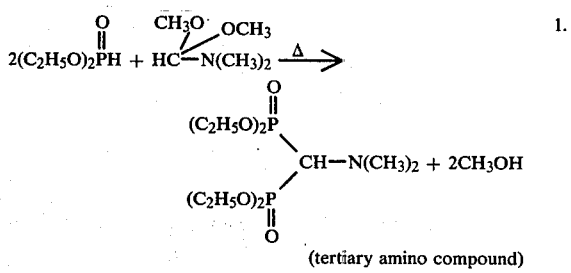

(tertiary amino compound)

2. quaternizing with dimethyl sulfate:

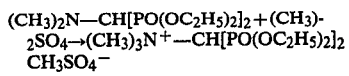

(viscous oil which solidifies into a white waxy solid upon standing).

These phosphonate ester starting materials may be varied by substituting other quaternizing agents such as the alkyl or aralkyl sulfates, iodides, chlorides, and bromides wherein the alkyl group may contain about 1 to 20 carbon atoms and the aralkyl group may be a benzyl group. Similarly other dialkyl formamide acetals may be used in equation 1 above, wherein each alkyl may independently be replaced by other alkyl groups containing about 1–20 carbon atoms. The quaternary ammonioalkylenediphosphonate ester salt is hydrolyzed in the presence of a hydrohalide such as hydrobromic acid to form the quaternary ammonioalkylenediphosphonate compound of instant invention, in accordance with the following equation:

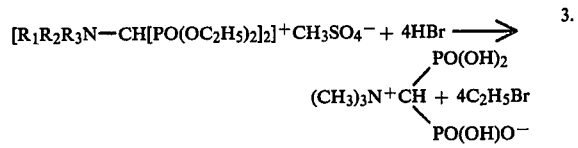

Other hydrohalides may be substituted for HBr such as HCl, or HI. One mole equivalent of the diphosphonate ester is reacted with at least 4 mole equivalents, and preferably in excess of 4 mole equivalents of the hydrohalide to ensure complete hydrolysis into the ethyl halide and the corresponding quaternary ammonioalkylenediphosphonate. The diphosphonate ester and the hydrohalide are refluxed for about one hour, at which time the theoretical amount of $C_2H_5Br$ is condensed and collected in a Dean-Stark trap.

The following examples illustrate the manner in which compounds of this invention are prepared but is not limited thereto.

EXAMPLE 1

Preparation of trimethylammoniomethylenediphosphonate:

$$(CH_3)_3N^+CH[PO(OH)_2PO(O^-)(OH)]$$

To 8.3 g (18 mmol) tetraethyl trimethylammoniomethylenediphosphonate methyl sulfate in a round bottom flask fitted with a Dean-Stark trap, condenser and dry ice condenser on top, was added 10 ml of 48% HBr (89 mmol). After heating and refluxing for 1 hour, 5.4 ml (72 mmol) of ethylbromide was collected in the Dean-Stark trap and the heating was stopped. The residual solution was cooled to room temperature, dripped into 300 ml of 2-propanol and a white sticky solid precipitated out. The precipitate was stirred in the propanol for 10–15 minutes and then permitted to settle out. The propanol was decanted from the sticky solid precipitate, and 300 ml methanol was added. This mixture was heated on a steam bath to boiling. The sticky solid slowly dissolved and then, while heating, spontaneously recrystallized. It took about 10–15 minutes for complete recrystallization. The crystalline white solid was filtered and dried in vacuum at 95°–100° C. The material titrates with sodium hydroxide as a tribasic acid; the first break occurred at pH 4.5, the second break at pH 8.5, and the third break at pH 11.0; and it has a melting point of 219°–219.5° C. (dec.).

Analysis for $C_4H_{13}NO_6P_2$:

|  | % P | (molecular weight) M.W. |
|---|---|---|
| Calculated: | 26.58 | 233.5 |
| Found: | 26.27 | 232.4 |

EXAMPLE 2

Preparation of dimethylaminomethylenediphosphonate for comparision with the quaternized analog of instant invention:

$$(CH_3)_2NCH[PO(OH)_2]_2$$

To 3.3 g (10 mmol) tetraethyl dimethylaminomethylenediphosphonate, as disclosed by H. Gross and B. Costisella, Angew. Chem. Internat. Edit. 7 391 (1968), was added 9.4 g (56 mmol) of 48% hydrobromic acid in an apparatus similarly equipped as in Example 1. The mixture was heated until no more ethyl bromide distilled out, about 3 hours. The residual solution was cooled to room temperature and dripped into 150 ml of 2-propanol. A precipitate formed. The propanol was decanted and the precipitate was washed with fresh propanol and filtered. The precipitate was slurried in 100 ml boiling methanol and dried at 95°–100° C. The precipitate did not dissolve and recrystallize in the boiling methanol as in Example 1. This solid also titrated as a tribasic acid and has a melting point of 225°–225.5° C. (dec.).

Analysis for $C_3H_{11}NO_6P_2$:

|  | % P | M.W. |
|---|---|---|
| Calculated: | 28.27 | 219.1 |
| Found: | 27.87 | 221.1 |

The process described in Example 1 may be varied by using other suitable alkanols to precipitate the quaternary ammonioalkylenediphosphonate and to wash the precipitate such as ethanol or butanol. Similarly other acidic materials may be used to hydrolyze the tetraethyl esters such as HCl, and HI. Other alkyl or aralkyl analogs of the trimethylammoniomethylenediphosphonates may be prepared by using tetraethyl esters of different quaternary ammoniomethylenediphosphonates such as triethylammonio-, dimethylethylammonio-, diethylmethyljammonio-, tripropylammonio-, dimethylpropylammonio-, dimethylbutylammonio-, dimethylpentylammonio-, dimethyloctylammonio-, dimethyldodecylammonio-, dimethylbenzylammonio-, dimethyloctadecylammonio-, and methylene-diphosphonate and the like. Also other esters may be hydrolyzed such as the tetramethyl, tetrapropyl or tetrabutyl esters of the quaternary ammoniomethylene diphosphonates.

Comparative in vitro tests with reference to the minimum concentration required to inhibit crystal growth of hydroxyapatite (the forerunner of calculus) yielded $1 \times 10^{-5}$ M for the product of Example 1 and $3 \times 10^{-5}$ M for the product of Example 2. Thus, it is apparent that instant novel compounds are three times more effective as an anti-calculus agent than the tertiary aminodiphosphonates. Furthermore, at $1 \times 10^{-4}$ M concentration, instant quaternary diphosphonates inhibit the crystal growth of hydroxyapatite by 12 hours.

Another essential feature of instant novel compounds is the greater capability of inhibiting staining due to cationic materials such as benzethonium chloride (BC). It was found that 4.2 mmol of Example 1 reduced stain 13 reflectance units, whereas 4.5 mmol of Example 2 is required to reduce stain only 10 units. The following table further illustrates the superior stain inhibition due to the presence of the quaternary ammonioalkylene diphosphonates using a mouthrinse containing 0.075% BC:

TABLE I

| Composition | Reflectance Units |
| --- | --- |
| 0.075% BC | 47 |
| 0.075% BC | 61 |
| 0.2% Ex. 1 | |
| 0.075% BC | 56 |
| 0.3% Ex. 1 | |
| Placebo | 57 |

Staining due to benzethonium chloride is evidenced by the decreased reflectance of hydroxylapatite powder after exposure to a BC mouthrinse, whereas in the presence of the quaternary ammonioalkylenediphosphonate the reflectance remains at the level of the placebo, indicating substantially complete stain inhibition.

The compounds of this invention may be used with pharmaceutical and oral carriers in dental creams, mouthrinses, or tooth powders at concentrations up to about 5% and in the pH range of 4 to 9, preferably at the pH found in the oral cavity, which is about 7.

When compounds of the instant invention are intended for use in compositions which inhibit the formation of oral calculus, they are typically incorporated in oral preparations in effective amounts up to about 5% by weight, preferably 0.05–1% by weight of the oral preparation. Typically, the oral preparation is a dentifrice, such as dental cream, tablet or powder, containing as a vehicle about 20–95% by weight of a water-insoluble polishing material, preferably including water-insoluble phosphate such as dicalcium phosphate, tricalcium phosphate, trimagnesium phosphate. the dentrifice may also include water; binders such as glycerine, sorbitol, propylene glycol 400; detergents; gelling agents such as Irish moss and sodium carboxy methyl cellulose; additional antibacterial agents; coloring or whitening agents; preservatives; silicones; chlorophyll compounds, additional ammoniated materials; flavoring or sweetening materials; and compounds which provide fluorine-containing ion such as sodium fluoride, stannous fluoride and sodium monofluorophosphate.

The oral preparation may also be a liquid such as mouth rinse which typically contains 20–99% by weight of an aqueous lower aliphatic alcohol, preferably having about 1–30% by weight alcohol such as ethanol, n-propyl, or isopropyl alcohol.

Such oral preparations are typically applied by brushing the teeth or rinsing the oral cavity for 30–90 seconds at least once daily. Typical oral preparations of the invention which can be applied in this manner are set forth below.

EXAMPLE 3

| Dental Cream | |
| --- | --- |
| | % |
| Trimethylammoniomethylenediphosphonate | 0.50 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |
| Water | 22.15 |
| pH 7.0 | |

*Tween 80-Polyoxyethylene (20 moles ethylene oxide) sorbitan monooleate.

EXAMPLE 4

0.50% of the dimethylethylammoniomethylenediphosphonate was used in lieu of the diphosphonate in Example 3.

EXAMPLE 5

| Mouthwash | |
| --- | --- |
| | % |
| Trimethylammoniomethylenediphosphonate | 0.25 |
| Benzethonium chloride | 0.075 |
| Nonionic detergent (pluronic F-68)* | 1.00 |
| Ethyl alcohol (containing Flavor) | 15.00 |
| Glycerine | 10.00 |
| Saccharin | 0.02 |
| Water | 73.655 |
| pH 6.3 | |

*Block polymer of 80% polyoxyethylene and 20% polyoxypropylene.

A preferred ingredient of instant composition is a nonionic organic surfactant which provides increased prophylactic action, assists in achieving thorough and complete dispersion of instant compositions throughout the oral cavity and renders instant compositions more cosmetically acceptable. The non-ionic surfactant imparts to the composition, detersive and foaming properties as well as maintains the flavoring materials in solution (i.e., solubilizes flavor oils). In addition, the non-ionics are completely compatible with the compounds of this invention, thereby providing for a stable, homogeneous composition of enhanced anti-bacterial, and anti-plaque activity.

The nonionic organic surface compounds which are contemplated are commercially known and comprise the water-soluble products which are derived from the condensation of an alkylene oxide or equivalent reactant and a reactive-hydrogen hydrophobe. The hydrophobic organic compounds may be aliphatic, aromatic or heterocyclic, although the first two classes are preferred. The preferred types of hydrophobes are higher aliphatic alcohols and alkyl phenols, although others may be used such as carboxylic acids, carboxamides, mercaptans, sulphonamides, etc. The ethylene oxide condensates with higher alkyl phenols represent a preferred class of nonionic compounds. Usually the hydrophobic moiety should contain at least about 6 carbon atoms, and preferably at least about 8 carbon atoms, and may contain as many as about 50 carbon atoms or more. The amount of alkylene oxide will vary considerably depending upon the hydrophobe, but as a general guide and rule, at least about 5 moles of alkylene oxide per mole of hydrophobe should be used. The upper limit of alkylene oxide will vary also, but no particular criticality can be ascribed thereto. As much as 200 or more moles of alkylene oxide per mole of hydrophobe may be employed. While ethylene oxide is the preferred and predominating oxyalkylating reagent, other lower alkylene oxides such as propylene oxide, butylene oxide, and the like may also be used or substituted in part for the ethylene oxide. Other nonionic compounds which are suitable are the polyoxyalkylene esters of the organic acids such as the higher fatty acids, the rosin acids, tall oil acids, acids from petroleum oxidation products, etc. These esters will usually contain from about 10 to about 22 carbon atoms in the acid moiety and from about 12 to about 30 moles of ethylene oxide or its equivalent.

Still other nonionic surfactants are the alkylene oxide condensates with the higher fatty acid amides. The fatty acid group will generally contain from about 8 to about 22 carbon atoms and this will be condensed with about 10 to about 50 moles of ethylene oxide as the preferred illustration. The corresponding carboxamides and sulphonamides may also be used as substantial equivalents.

Still another class of nonionic products are the oxyalkylated higher aliphatic alcohols. The fatty alcohols should contain at least 6 carbon atoms, and preferably at least 8 carbon atoms. The most preferred alcohols are lauryl, myristyl, cetyl, stearyl and oleyl alcohols and the said alcohols should be condensed with at least about 6 moles of ethylene oxide, and preferably about 10 to 30 moles of ethylene oxide. A typical nonionic product is oleyl alcohol condensed with 15 moles of ethylene oxide. The corresponding alkyl mercaptans when condensed with ethylene oxide are also suitable in the compositions of the present invention.

The amount of non-ionic may generally be varied from about 0.2-3.0% by weight of the total formulation, depending on the specific nature of the non-ionic utilized as well as on the amounts and nature of the other ingredients in the oral formulation.

The oral formulations may also contain cationic antibacterial agents with which the quaternary phosphonates are completely compatible, in amounts of about 0.01-5%. Typical examples of such agents are guanidines, biguanides and amines such as:

N$^1$-(4-chlorobenzyl)-N$^5$-2,4-(dichlorobenzyl)biguanide;
p-chlorophenyl biguanide;
4-chlorobenzhydryl biguanide;
4-chlorobenzhydrylguanylurea;
N$^1$-3-lauroxypropyl-N$^5$-p-chlorobenzylbiguanide;
1,6-di-p-chlorophenylbiguanidohexane;
1-(lauryldimethylammonium)-8-(p-chlorobenzyldimethylammonium) octane dichloride;
5,6-dichloro-2-guanidinobenzimidazole;
N$^1$-p-chlorophenyl-N$^5$-laurylbiguanide;
5-amino-1, 3-bis(2-ethoxyhexyl)-5-methylhexahydropyrimidine;
Chlorhexidine
Benzethonium chloride
Cetyl pyridinium chloride and their non-toxic acid addition salts.

Although this invention has been described with reference to specific examples, it will be apparent to one skilled in the art that various modifications may be made thereto which fall within its scope.

What is claimed is:

1. A non-staining and stain-inhibiting anticalculus oral composition comprising an oral vehicle containing a non-staining and stain-inhibiting amount of an anticalculus agent selected from the group consisting of a quaternary ammonium alkylene diphosphonate having the structural formula:

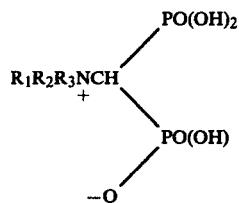

wherein $R_1$, $R_2$ and $R_3$ are each independently an alkyl group containing from 1 to about 20 carbon atoms or an aralkyl group wherein the aryl radical is a phenyl and the alkyl radical contains 1–8 carbon atoms, and its pharmaceutically acceptable salts, and a dental-staining cationic antibacterial agent, said agent being present in amount of about 0.01 to 5% by weight, with which said anticalculus agent is completely compatible, said anticalculus agent being effective to inhibit dental stain formation otherwise caused by said antibacterial agent.

2. The oral composition according to claim 1 which additionally contains about 0.2–3% by weight of a nonionic organic surfactant.

3. The oral composition according to claim 1, wherein the anticalculus agent is a quaternary ammonium alkylene diphosphonate salt selected from the group consisting of alkali metals, alkaline earth metals, ammonium and low molecular weight substituted ammonium salts.

4. The oral composition in accordance with claim 1, wherein the anticalculus agent is trimethylammoniomethylene diphosphonate.

5. A non-staining method of inhibiting the formation of dental calculus which comprises treating the oral cavity with an oral composition containing a non-staining and stain-inhibiting amount of the anticalculus agent selected from the group consisting of a quaternary ammonium alkylene diphosphonate having the structural formula:

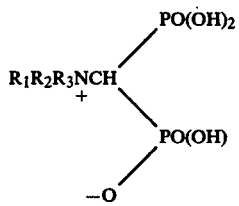

wherein $R_1$, $R_2$ and $R_3$ are each independently an alkyl group containing from 1 to about 20 carbon atoms or an aralkyl group wherein the aryl radical is a phenyl and the alkyl radical contains 1–8 carbon atoms, and its pharmaceutically acceptable salts.

6. A non-staining method of inhibiting the formation of dental calculus in accordance with claim 5 which comprises brushing the teeth.

7. A non-staining method of inhibiting the formation of dental calculus in accordance with claim 5 which comprises rinsing the oral cavity.

* * * * *